United States Patent
McAleer et al.

(10) Patent No.: US 7,807,031 B2
(45) Date of Patent: *Oct. 5, 2010

(54) DISPOSABLE TEST STRIPS WITH INTEGRATED REAGENT/BLOOD SEPARATION LAYER

(75) Inventors: Jerome F. McAleer, Wantage (GB); Manuel Alvarez-Icaza, Inverness (GB); Geoff Hall, Inverness (GB); Elliot V. Plotkin, Inverness (GB); David Scott, Witney Oxon (GB); Oliver W. H. Davies, Inverness (GB)

(73) Assignee: Diabetes Diagnostics, Inc., Waltham, MA (US)

( * ) Notice: Subject to any disclaimer, the term of this patent is extended or adjusted under 35 U.S.C. 154(b) by 1149 days.

This patent is subject to a terminal disclaimer.

(21) Appl. No.: 11/453,174

(22) Filed: Jun. 13, 2006

(65) Prior Publication Data

US 2006/0260940 A1    Nov. 23, 2006

Related U.S. Application Data

(63) Continuation of application No. 09/869,887, filed as application No. PCT/US00/00620 on Jan. 11, 2000, now Pat. No. 7,112,265, which is a continuation-in-part of application No. 09/228,855, filed on Jan. 12, 1999, now Pat. No. 6,241,862, which is a continuation-in-part of application No. 09/005,710, filed on Jan. 12, 1998, now Pat. No. 5,951,836, which is a continuation of application No. 08/601,223, filed on Feb. 14, 1996, now Pat. No. 5,708,247.

(51) Int. Cl.
*G01N 27/327* (2006.01)

(52) U.S. Cl. .............................. 204/403.05; 204/403.06

(58) Field of Classification Search .................. 204/403.01–403.15; 205/777.5, 778, 792
See application file for complete search history.

(56) References Cited

U.S. PATENT DOCUMENTS 4,195,129 A    3/1980    Fukui et al.

(Continued)

FOREIGN PATENT DOCUMENTS

EP    0286118    10/1988

(Continued)

OTHER PUBLICATIONS

English abstract of JP55010583 "Enzyme Electrode and its Manufacture" Shiro Nankai et al., Jan. 25, 1980.

(Continued)

*Primary Examiner*—Alex Noguerola

(57) ABSTRACT

An improved disposable glucose test strip for use in a test meter of the type which receives a disposable test strip and a sample of blood from a patient and performs an electrochemical analysis is made using a non-conductive integrated reagent/blood separation layer containing a filler, an enzyme effective to oxidize glucose, e.g., glucose oxidase, and a mediator effective to transfer electrons from the enzyme. The integrated layer formulation is printed over a conductive carbon element to form a working electrode. The filler, for example a silica filler, is selected to have a balance of hydrophobicity and hydrophilicity such that one drying it forms a two-dimensional network on the surface of the conductive element. The response of this test strip is essentially temperature independent over relevant temperature ranges and is substantially insensitive to the hematocrit of the patient.

10 Claims, 9 Drawing Sheets

U.S. PATENT DOCUMENTS

| | | |
|---|---|---|
| 4,418,148 A | 11/1983 | Oberhardt |
| 4,655,880 A | 4/1987 | Liu |
| 4,876,205 A | 10/1989 | Green et al. |
| 4,966,671 A | 10/1990 | Nylander et al. |
| 5,120,420 A | 6/1992 | Nankai et al. |
| 5,124,253 A | 6/1992 | Foulds et al. |
| 5,126,034 A | 6/1992 | Carter et al. |
| 5,141,868 A | 8/1992 | Shanks et al. |
| 5,185,256 A | 2/1993 | Nankai et al. |
| 5,262,035 A | 11/1993 | Gregg et al. |
| 5,264,106 A | 11/1993 | McAleer et al. |
| 5,286,362 A | 2/1994 | Hoenes et al. |
| 5,288,636 A | 2/1994 | Pollman et al. |
| 5,378,628 A | 1/1995 | Gratzel et al. |
| 5,437,999 A | 8/1995 | Diebold et al. |
| 5,565,085 A | 10/1996 | Ikeda et al. |
| 5,582,697 A | 12/1996 | Ikeda et al. |
| 5,582,698 A | 12/1996 | Flaherty et al. |
| 5,601,694 A | 2/1997 | Maley et al. |
| 5,628,890 A | 5/1997 | Carter et al. |
| 5,658,444 A | 8/1997 | Black et al. |
| 5,708,247 A | 1/1998 | McAleer et al. |
| 5,762,770 A | 6/1998 | Pritchard |
| 5,951,836 A | 9/1999 | McAleer et al. |
| 6,241,862 B1 * | 6/2001 | McAleer et al. ........ 204/403.05 |

FOREIGN PATENT DOCUMENTS

| | | |
|---|---|---|
| EP | 0289269 | 11/1988 |
| EP | 0170375 B1 | 5/1990 |
| EP | 0207370 B1 | 4/1993 |
| EP | 0127958 B2 | 4/1996 |
| WO | WO 89/08713 A1 | 9/1989 |
| WO | WO 94/27140 A1 | 11/1994 |
| WO | WO 97/00441 | 1/1997 |
| WO | WO 97/02487 A1 | 1/1997 |
| WO | WO 98/35225 | 8/1998 |
| WO | WO 99/19507 | 4/1999 |

OTHER PUBLICATIONS

English abstract of JP55010584 "Enzyme Electrode and its Manufacture" Shiro Nankai et al., Jan. 25, 1980.

English abstract of JP55010581 "Enzyme Electrode" Shiro Nankai et al., Jan. 25, 1980.

English abstract of JP55124060 "Enzyme Electrode" Shiro Nankai et al., Jan. 24, 1980.

European Search Report, Munich, Germany, May 30, 2006, re European Application 05015727.0.

European Search Report, Munich, Germany, May 31, 2006, re European Application 05015728.8.

European Search Report, Munich, Germany, May 31, 2006, re European Application 05015729.6.

* cited by examiner

DISPOSABLE TEST STRIPS WITH INTEGRATED REAGENT/BLOOD SEPARATION LAYER

CROSS-REFERENCE TO RELATED APPLICATIONS

This application is a continuation application of Ser. No. 09/869,887 filed Feb. 20, 2002 now U.S. Pat. No. 7,112,265, which is a national stage filing under 371 of international application no. PCT/US00/00620 filed on Jan. 11, 2000, which is a continuation-in-part application of Ser. No. 09/228,855 filed on Jan. 12, 1999, now U.S. Pat. No. 6,241,862, which is a continuation-in-part application of Ser. No. 09/005,710 filed on Jan. 12, 1998, now U.S. Pat. No. 5,951,836, which is a continuation application of Ser. No. 08/601,223 filed on Feb. 14, 1996, now U.S. Pat. No. 5,708,247. The complete disclosures of the aforementioned related U.S. patent applications are hereby incorporated herein by reference for all purposes.

BACKGROUND OF THE INVENTION

This application relates to disposable test strips for use in electrochemical determinations of blood analytes such as glucose, and to methods and compositions for use in making such strips.

Glucose monitoring is a fact of everyday life for diabetic individuals, and the accuracy of such monitoring can literally mean the difference between life and death. To accommodate a normal life style to the need for frequent monitoring of glucose levels, a number of glucose meters are now available which permit the individual to test the glucose level in a small amount of blood.

Many of these meters detect glucose in a blood sample electrochemically, by detecting the oxidation of blood glucose using an enzyme such as glucose oxidase provided as part of a disposable, single-use electrode system. Examples of devices of this type are disclosed in European Patent No. 0 127 958, and U.S. Pat. Nos. 5,141,868, 5,286,362, 5,288,636, and 5,437,999 which are incorporated herein by reference for purposes of those countries which permit such incorporation.

In general, existing glucose test strips for use in electrochemical meters comprise a substrate, working and reference electrodes formed on the surface of the substrate, and a means for making connection between the electrodes and the meter. The working electrode is coated with an enzyme capable of oxidizing glucose, and a mediator compound which transfers electrons from the enzyme to the electrode resulting in a measurable current when glucose is present. Representative mediator compounds include ferricyanide, metallocene compounds such as ferrocene, quinones, phenazinium salts, redox indicator DCPIP, and imidazole-substituted osmium compounds.

Working electrodes of this type have been formulated in a number of ways. For example, mixtures of conductive carbon, glucose oxidase and a mediator have been formulated into a paste or ink and applied to a substrate. EP 0 127 958 and U.S. Pat. No. 5,286,362. In the case of disposable glucose strips, this application is done by screen printing in order to obtain the thin layers suitable for a small flat test strip. The use of screen printing, however, introduces problems to the operation of the electrode.

Unlike a thicker carbon paste electrode which remains fairly intact during the measurement, screen printed electrodes formed from carbon pastes or inks are prone to break up on contact with the sample. The consequences of this breakup are two-fold. Firstly, the components of the electrode formulation are released into solution. Once these components drift more than a diffusion length away from the underlying conductive layer, they no longer contribute toward the measurement, but in fact diminish the response by depleting inwardly-diffusing analyte. Secondly, the breakup of the screen printed electrode means that the effective electrode area is falling over time.

The combination of these two effects results in current transients which fall rapidly from an initial peak over the period of the measurement, and a high sensitivity to oxygen which quickly competes with the mediator for the enzyme. This fact is clearly demonstrated by the much lower currents measured in blood samples than in plasma samples or other aqueous media, and can result in erroneous readings. A further consequence is that the transients are often "lumpy" as the electrode breaks up in a chaotic manner. Lumpy transients either give rise to erroneous readings or rejected strips, neither of which are acceptable.

In addition to the potential for electrode breakup of screen-printed carbon-based electrodes, known electrodes used in disposable glucose test strips have been kinetically-controlled, i.e., the current depends on the rate of conversion of glucose by the enzyme. Because the response measured by the instrument represents a balance between the reactions of enzyme and mediator, enzyme and glucose and enzyme and oxygen, and because each of these reactions has its own dependence on temperature, the response of a kinetically-controlled test strip is very sensitive to the temperature of the sample. Substantial variation in the measured glucose value can therefore occur as a result of variations in sample handling.

A further challenge facing sensors for electrochemical glucose detection arises as a result of interference from blood cells present in the sample. The level of red blood cells is reflected in the hematocrit reading. Typically, high hematocrit samples results in readings that are lower than the true value, while low hematocrit samples result in readings that are higher because the blood cells tend to foul the surface of the electrode and limit electron transfer. Also, oxygen bound to the hemoglobin of red blood cells competes with the mediator for the reduced enzyme, thereby further diminishing the glucose response. Attempts have been made to limit the hematocrit effect by adding a membrane to filter out blood components (see, U.S. Pat. No. 5,658,444, which is incorporated herein by reference for purposes of those countries which permit such incorporation), but this adds an extra step to the manufacturing process, with associated increase in cost and often degraded performance in other areas such as precision.

Because of the importance of obtaining accurate glucose readings to the well-being of a patient using the meter and disposable test strips, it would be highly desirable to have a glucose test strip which did not suffer from these drawbacks, and which therefore provided a more consistent and reliable indication of actual blood glucose values, regardless of actual conditions. It is therefore an object of the present invention to provide disposable glucose test strips which provide a glucose reading that is essentially independent of the hematocrit of the sample, an which include an integrated reagent/blood separation layer.

It is further object of the present invention to provide an improved method for making disposable glucose test strips.

SUMMARY OF THE INVENTION

The present invention provides an improved disposable test strip for use in a test meter of the type which receives a disposable test strip and a sample of blood from a patient and performs an electrochemical analysis of the amount of a blood analyte such as glucose in the sample. The test strip comprises:

(a) a substrate;

(b) a first conductive element disposed on the substrate;

(c) a second conductive element disposed on the substrate in sufficient proximity to the first conductive element to allow the completion of an electrical circuit between the first and second conductive elements when a sample of blood is placed on the test strip;

(d) a non-conductive integrated reagent/blood separation layer disposed over the first conductive element; and (e) contacts for making an electrical connection between the first and second conductive elements and the test meter. The integrated reagent/blood separation layer comprises reagents for the electrochemical detection of the analyte dispersed in a non-conductive matrix effective to exclude blood cells from the surface of the first conductive element while permitting access to the first conductive element by soluble electroactive species. In one embodiment of the invention, a glucose test strip is formed with an integrated reagent/blood separation layer comprising a filler which has both hydrophobic and hydrophilic surface regions, an enzyme effective to oxidize glucose, e.g., glucose oxidase, and a mediator effective to transfer electrons from the enzyme to the conductive element. The filler is selected to have a balance of hydrophobicity and hydrophilicity such that on drying the integrated reagent/blood separation layer forms a two-dimensional network on the surface of the conductive element. Preferred integrated reagent/blood separation layers comprise non-conductive silica fillers in combination with materials such as hydroxyethyl cellulose (HEC). The silica and HEC form a two-dimensional network which excludes red blood cells, thus rendering the test strip substantially insensitive to the hematocrit of the patient.

In a preferred embodiment of the invention, the test strips are prepared with an insulation layer disposed over at least the first conductive element. This insulation layer has an aperture formed in it which is aligned with a portion of the first conductive element, and the integrated reagent/blood separation layer is disposed to make contact with the first conductive element through this aperture.

DETAILED DESCRIPTION OF THE INVENTION

Figure 1A:
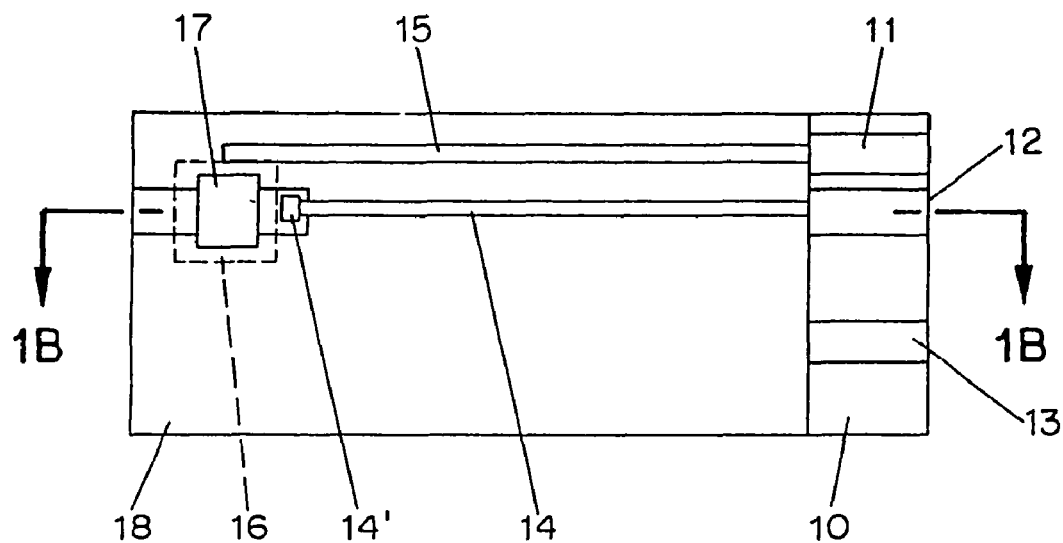
FIGS. 1A and 1B show an electrode structure useful in a disposable test strip in accordance with the invention.
Figure 1B:
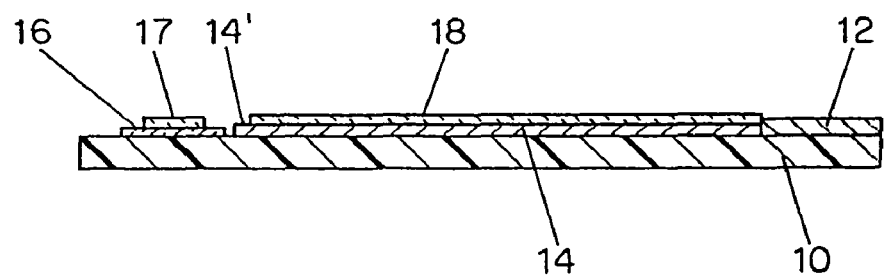

FIGS. 1A and 1B show electrodes useful in a disposable test strip in accordance with the invention. As shown, the electrodes are formed on a substrate 10. On the substrate 10 are placed two conductive elements 14' and 16, connected by leads 14 and 15 to conductive contacts 11, 12; and 13. An insulating mask 18 is then formed, leaving at least a portion of conductive elements 14' and 16, and the contacts 11, 12 and 13 exposed. A non-conductive integrated reagent/blood separation layer 17 is then applied over the insulating mask 18 to make contact with conductive element 16.

Figure 2:
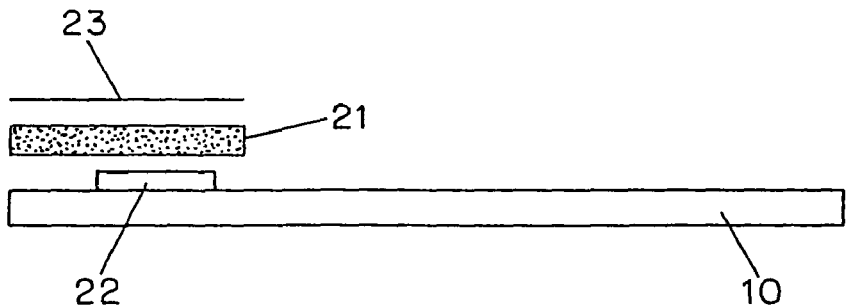
FIG. 2 shows a test strip in accordance with the invention.

The assembly shown in FIG. 1 provides a fully functional assembly for the measurement of a blood analyte when connected to a meter. Advantageously, however, the electrode strips of the invention are finished by applying a nylon or polyester mesh 21 over the sample application region defined by the location of the integrated reagent/blood separation layer 17 of the electrode assembly 22, and then a top cover 23 to prevent splashing of the blood sample. (FIG. 2) The polyester mesh acts to guide the sample to the reference electrode, conductive element 14', thereby triggering the device and initiating the test.

The utilization of a non-conductive integrated reagent/blood separation layer provides an important distinction from and advantage over known test strips which utilize a conductive reagent-containing slurry to print the reagents. In these systems, the printed slurry becomes a functional part of the electrode and charge transfer can take place at the outer surface of the reagent layer. If the layer is in direct contact with blood, i.e., when no intervening separation layer has been deposited, red and white blood cells, fat and proteins present in the sample can interact with the reagent layer and interfere with the measurement of the amount of analyte in the sample.

In contrast, in the present invention, the integrated reagent/blood separation layer is non-conductive, and thus is not a part of the electrode either structurally or functionally. Change transfer does not occur unless electroactive species pass through the openings/pores of the integrated reagent/blood separation layer to reach the underlying conductive element. Thus, the integrated reagent/blood separation layer provides a barrier to the passage of interferents such as cells and macromolecules to the conductive element resulting in a device with superior properties that is simpler to make.

Figure 9A:
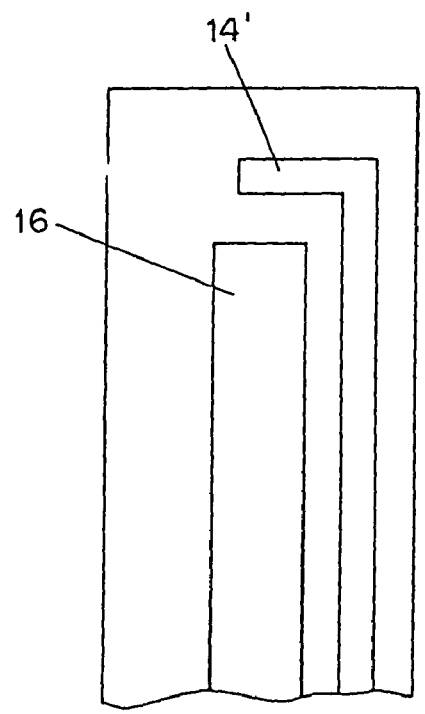
FIGS. 9A-C show a three-step process for manufacture of test strips in accordance with the invention.
Figure 9B:
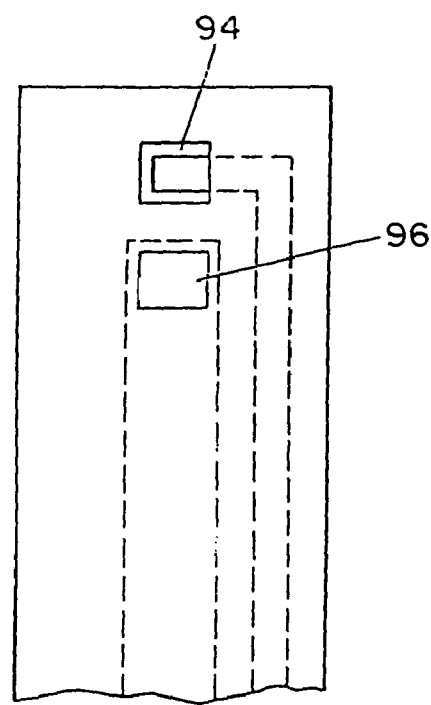
Figure 9C:
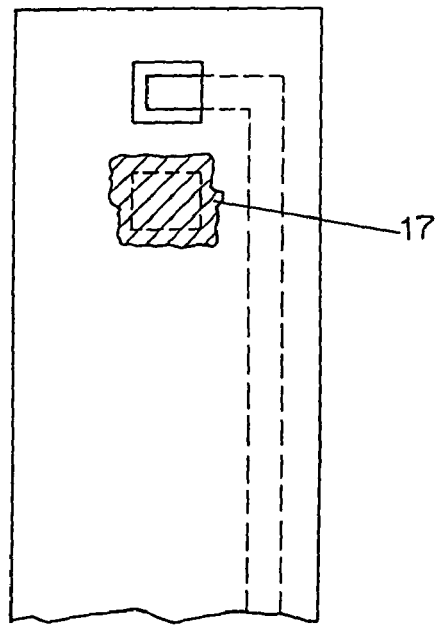

In achieving this result, it is particularly desirable that the integrated reagent/blood separation layer be deposited in such a way that no portion of the conductive element 16 be directly exposed to the sample when it is placed in the sample application region. The methodology described above, in which an insulating layer with apertures providing access to the conductive elements 14' and 16 is utilized is particularly suited for achieving this result. Thus, as shown in FIGS. 9A-C, this methodology allows the formation of the test strip in only three steps. In the first step (FIG. 9A), two conductive elements 14' and 16 and associated leads and contacts are deposited on a substrate. In a second step (FIG. 9B), a layer of insulating material is deposited over the conductive elements. The insulating material has two apertures 94 and 96, one in alignment with each of the conductive elements 14' and 16. In the third step, (FIG. 9C), the integrated reagent/blood separation layer 17 is deposited over the aperture 96. By making the deposited layer 17 larger in dimensions than the aperture 96, the reagent layer completely covers the underlying conductive element and that it is not exposed directly to the sample, thereby providing effective blood separation.

The complete coverage of conductive element 16 also addresses another sources of error which can occur as a result of electrochemical oxidation or small molecules such as ascorbic acid, uric acid and acetaminophen which may be present in the sample. When present, the oxidation of these molecules at the surface of the electrode leads to spuriously elevated current levels, and thus an inaccurate measurement of the desired analyte, e.g. glucose. The integrated reagent/blood separation layer of invention will not generally exclude these molecules, since they are small compared to the pore sizes observed. However, by including a pH buffer in the integrated reagent/blood separation layer one can shift the local pH at the electrode surface to a level where electrochemical potential of these species is higher. Thus, for example, the use of an integrated reagent/blood separation layer in which the pH is buffered to a level of around pH 5 will substantially reduce the impact of these interferents. To maximize the effectiveness of this buffering, however, the entire conductive element must be covered, since even a relatively small region of exposed (not buffered) electrode surface can result in a large interference current.

Not only do the test strips of the invention provide performance benefits resulting from the separation of the conductive element from the blood sample, the test strips of the invention are also resistant to other sources of error. For example, during the period of a test, reagents may diffuse laterally away from the original deposit. If the reagent layer is deposited directly on the conductive element, these reagents will continue to contribute to the measured signal. Any variations in convective diffusion from test to test (for example as a result of differences in temperature or differences in the handling of the instrument) will therefore be manifested as irreproducibility in the signal. If the reagent layer overlaps the insulation print, however, lateral diffusion away from the aperture will not contribute to the signal and therefore will not give rise to variations in the signal.

In addition to providing a test strip with beneficial properties, the methodology outlines in FIGS. 9A-C offers several advantages from a manufacturing perspective. First, if the reagent layer is printed directly onto the conductive element, the "active area" is defined by the area of the reagent layer. The precision of the test is therefore determined by the precision with which the reagent layer can be printed. In contrast, by first depositing an apertured insulation layer defining the region of the contact between the reagent layer and the underlying conductive element, the active area is defined by the size of the aperture in the insulation layer. Since insulation layers are typically printed using a finer screen, much better edge definition, and thus greater device precision can be achieved. Thus, neither the area of conductive element 16 nor of the integrated reagent/blood separation layer are critical to the performance characteristics of the finished test strip. The conductive elements and the integrated reagent/blood separation layer may therefore be applied using techniques which provide less precision than can be employed in other processes.

It will be appreciated by persons skilled in the art that, while both conductive elements must be accessible to electroactive species in a sample disposed in the sample application region, the important function of the insulation mask is to provide an aperture defining the contact region between conductive element 16 and the integrated reagent/blood separation layer 17. Thus, in the limiting case, it is only necessary to form one aperture in the insulation layer. The second conductive element can be exposed along an edge of the insulation layer, or may be located on a facing surface in a folded electrode structure.

The substrate 10 used in making the test strips of the invention can be any non-conducting, dimensionally stable material suitable for insertion into a glucose test meter. Suitable materials include polyester films, for example a 330 micron polyester film, and other insulating substrate materials such as polyvinyl chloride (PVC) and polycarbonate.

The conductive elements and associated leads and contacts can be formed from essentially any conductive material including silver, Ag/AgCl, gold, or platinum/carbon, and need not all be formed from the same material. The conductive element 16 is preferably formed from conductive carbon. Preferred conductive carbon are ERCON ERC1, ERCON ERC2 and Acheson Carbon Electrodag 423. Carbon with these specifications is available from Ercon Inc. (Waltham, Mass., USA), or Acheson Colloids, (Princes Rock, Plymouth, England). The conductive element 16 makes contact with working electrode track 15, and is close to, but not contacting conductive element 14' disposed as the end of reference electrode track 14.

The insulating layer 18 can be formed from polyester-based printable dielectric materials such as ERCON R488-B (HV)-B2 Blue. The top cover 23 is suitably formed from a polyester strip or a "hot melt" coated plastic.

The test strips of the present invention do not require the formation of a discrete exit port to permit air to escape from the device as sample enters the electrode chamber but instead uses a distributed exit along all of the edges of the mesh. As the sample fluid wicks along the mesh, air seeps out of the edges of the mesh all around the device underneath the top layer. The sample fluid does not seep out because the insulation layer imparts significant hydrophobicity to that part of the mesh. The liquid sample therefore remains in the central hydrophilic region.

The key to the performance achieved using the present invention is in the nature of the integrated reagent/blood separation layer 17. This layer can be formed from a mixture containing a filler which has both hydrophobic and hydrophilic surface regions, and in the case of a glucose test strip, an enzyme which can oxidize glucose, and a mediator which can transfer electrons from the enzyme to the underlying conductive element layer 16. This layer is suitably formed by formulating an ink which contains the filler, the enzyme and the mediator in a suitable carrier and using this ink to print the layer 17 onto the device.

A preferred filler for use in the layer 17 is silica. Silica is available in a variety of grades and with a variety of surface modifications. While all silica compounds tested resulted in a product which could measure glucose under some conditions, the superior performance characteristics of glucose test strip of the invention are obtained when a silica having a surface modification to render it partially hydrophobic is used. Materials of this type include Cab-O-Sil TS610, a silica which is modified by partial surface treatment with methyl dichlorosilane; Cab-o-Sil 530, a silica which is modified by full surface treatment with hexamethyl disilazane; Spherisorb C4 silica, which is surface modified with 4 carbon chains; and other similarly modified silicas; or combinations thereof. Silica with a surface modification which is too hydrophobic should be avoided. For example, it has been observed that C18-modified silica is too hydrophobic to form a printable ink.

During the process of manufacturing the ink of the invention, the particles are broken down by homogenization to expose hydrophilic inner portions of the silica particles. The actual particles present in the ink therefore have both hydrophilic and hydrophobic regions. The hydrophilic regions form hydrogen bonds which each other and with water.

When this material is formulated into an ink as described below in Example 1, and screen printed onto the conductive element 16, the dual nature of the material causes it two form layers of two-dimensional networks which take from as a kind of honeycomb which is visible upon microscopic examination. On rehydration; this layer does not break up, but swells to form a gelled reaction zone in the vicinity of the underlying conductive element 16. Reactants such as enzyme, mediator and glucose move freely within this zone, but interfering species such as red blood cells containing oxygenated hemoglobin are excluded. This results in a device in which the amount of current generated in response to a given amount of glucose varies by less than 10 percent over a hematocrit range of 40 to 60%, and which is thus substantially insensitive to the hematocrit of the sample, and in fact performs substantially the same in blood as in a cell-free control solution. (FIGS. 3A-C, FIG. 4 and FIG. 5A-5C)

Figure 6A:
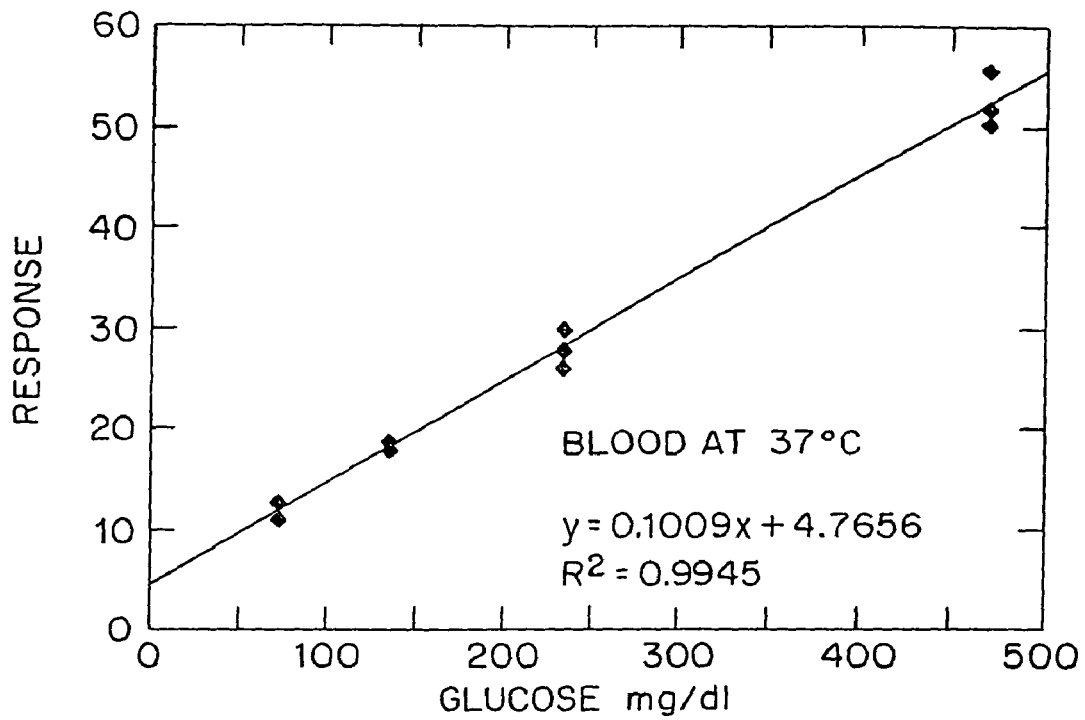
FIGS. 6A and 6B show the current measured as a function of glucose at two different temperatures.
Figure 6B:
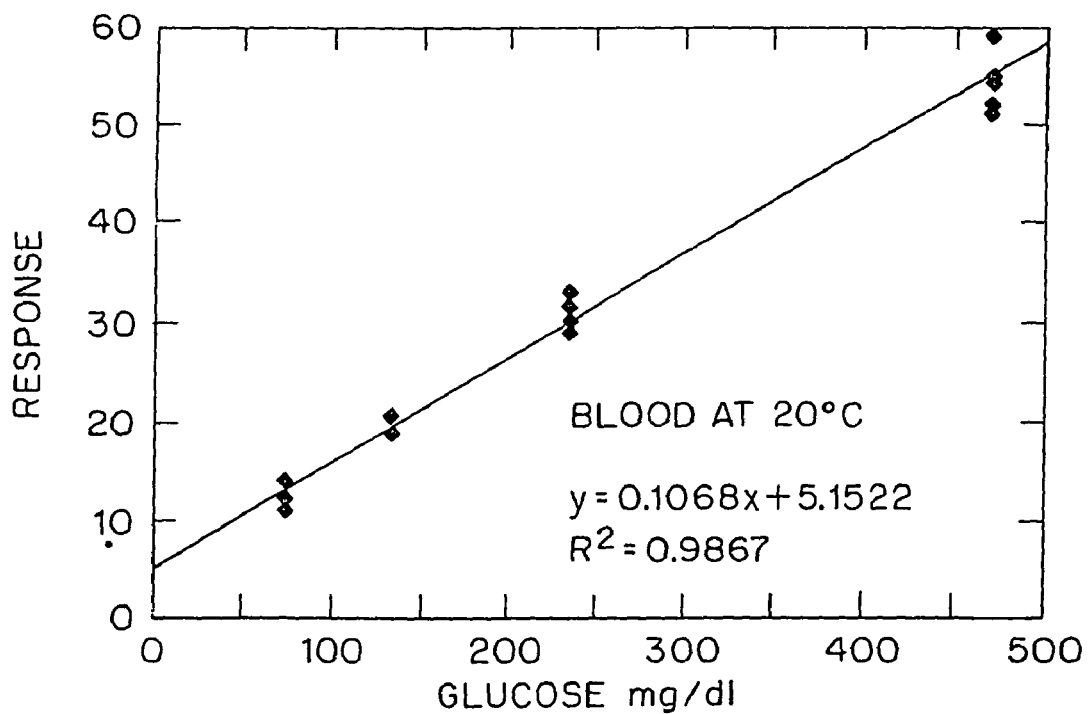

Furthermore, the gelled reaction zone presents a greater barrier to entry of blood analytes such as glucose which makes the device diffusion, rather than kinetically limited. This leads to a device in which the measured current varies by less than 10 percent over a temperature range from 20° C. to 37° C. and which is thus essentially temperature independent. (FIGS. 6A and 6B)

When making a glucose test strip, the integrated reagent/blood separation layer is advantageously formed from an aqueous composition containing 2 to 10% by weight, preferably 4 to 10% and more preferably about 4.5% of a binder such as hydroxyethylcellulose or mixtures of hydroxyethylcellulose with alginate or other thickeners; 3 to 10% by weight, preferably 3 to 5% and more preferably about 4% silica; 8 to 20% by weight, preferably 14 to 18% and more preferably about 16% of a mediator such as ferricyanide; and 0.4 to 2% by weight, preferably 1 to 2% and more preferably about 1.6% of an enzyme such as glucose oxidase, assuming a specific activity of about 250 units/mg, or about 1000 to 5000 units per gram of ink formulation.

The integrated reagent/blood separation layer may also include additional ingredients without departing from the scope of the invention. For example, the nonconducting layer may include an antifoam. In addition, the nonconducting layer may be formulated with a buffering agent to control the pH of the reaction zone. The pH may be maintained at a level within the range from about pH 3 to pH 10. In one embodiment of the invention, it is of particular utility to maintain the pH of the device at a level above 8 because at this pH oxygen bound to hemoglobin is not released. Further, at this pH, the reaction rate of glucose oxidase with oxygen is very low. Thus, selection of an appropriate pH can further stabilize the performance of the test strip against the effects of varying hematocrit. In an alternative embodiment of the invention, maintaining a low pH (below pH 5.5, the optimum pH for reaction of glucose oxidase with oxygen) may be preferred. For example, maintaining a pH of around pH 5 is better if the primary concern is the elimination of electrochemical interferences arising from oxidation of interfering substances such as ascorbic acid, uric acid or acetaminophen, since these compounds are more difficult to oxidize at lower pH.

While a preferred embodiment of the invention is a glucose test strip as described above, the test strips of the invention are not limited to the detection of glucose. For example, a fructosamine test strip could include two layers disposed over the conductive element. The first, lower layer is formed from an ink comprising a carbonate buffer (pH>10) in a silica mix substantially as described in Example 7 but without enzyme, mediator or citrate buffer. The second, upper layer is formed from an ink further comprising an oxidant such as ferricyanide.

Figure 7:
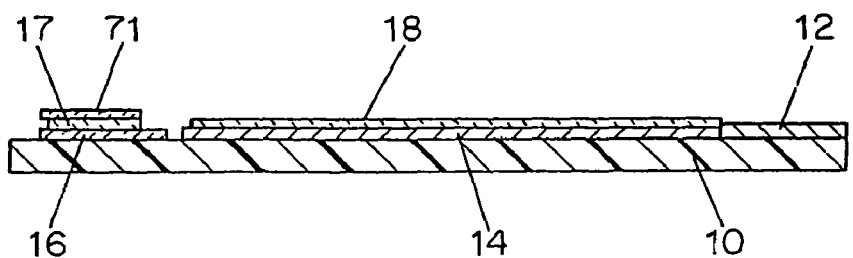
FIG. 7 shows a further embodiment of a glucose test strip according to the invention.

FIG. 7 shows an alternative embodiment of the invention. In this embodiment, a second non-conductive layer 71 is disposed over the integrated reagent/blood separation layer 17. This layer is formed from a composition which is identical to the first integrated reagent/blood separation layer except that the enzyme or both the enzyme and the mediator are omitted. This layer further isolates the conductive element 16 from contact with oxygen-carrying red blood cells, thus reducing the effects of oxygen. Furthermore, to the extent that enzyme may tend to diffuse away from the surface of the electrode during the course of the measurement such a layer containing mediator can provide an increased region in which it will have mediator available for the transfer of electrons.

EXAMPLE 1

A non-conducting formulation for preparation of the integrated reagent/blood separation layer 17 was made as follows. 100 ml of 20 mM aqueous trisodium citrate was adjusted to pH 6 by the addition of 0.1 M citric acid. To this 6 g of hydroxyethyl cellulose (HEC) was added and mixed by homogenization. The mixture was allowed to stand overnight to allow air bubbles to disperse and then used as a stock solution for the formulation of the coating composition.

2 grams Cab-o-Sil TS610 silica and 0.1 grams of Dow Corning antifoam compound was gradually added by hand to 50 grams of the HEC solution until about ⅘ of the total amount had been added. The remainder was added with mixing by homogenization. The mixture was then cooled for ten minutes in a refrigerator. 8 g of potassium hexacyanoferrate (III) was then added and mixed until completely dissolved. Finally, 0.8 g of glucose oxidase enzyme preparation (250 Units/mg) was added and then thoroughly mixed into the solution. The resulting formulation was ready for printing, or could be stored with refrigeration.

EXAMPLE 2

To prepare glucose test strips using the ink formulation of Example 1, a series of patterns are used to screen print layers onto a 330 micron polyester substrate (Melinex 329). The first step is the printing of carbon pads. An array of 10×50 pads of carbon is formed on the surface of the polyester substrate by printing with EC2 carbon. (Ercon) The printed substrate is then passed through a heated dryer, and optionally cured at elevated temperature (e.g. 70° C.) for a period of 1 to 3 weeks.

Next, an array of silver/silver chloride connecting tracks and contacts is printed onto the substrate using ERCON R-414 (DPM-68) 1.25 bioelectrode sensor coating material and dried. One working track which makes contact with the carbon pad and one reference track is printed for each carbon pad in the array.

A dielectric layer is then printed using ERCON R488-B (HV)-B2 Blue and dried. The dielectric layer is printed in a pattern which covers substantially all of each device, leaving only the contacts, the tip of the reference electrode and the carbon pads uncovered.

On top of the dielectric layer the ink of Example 1 is used to form a integrated reagent/blood separation layer overlaid on top of each conductive carbon pad.

Polyester mesh strips (Scryncl PET230 HC) are then laid down across the substrate in lines, covering the reactions areas exposed by the windows in the dielectric. An 5 mm wide polyester strip (50 microns thick) is then applied over the top of the mesh strips, and the edges of the electrodes are heat sealed. Finally, the substrate is cut up to provide 50 individual electrodes, for example having a size of 5.5 mm wide and 30 mm long.

EXAMPLE 3

Figure 4:
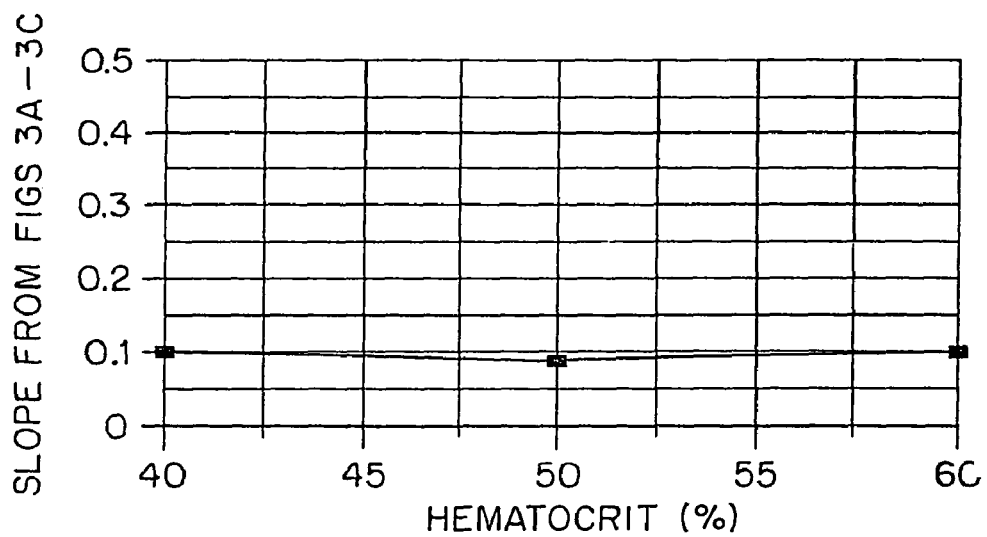
FIG. 4 shows the relationship of the glucose-concentration dependence of the measured current as a function of hematocrit.
Figure 3A:
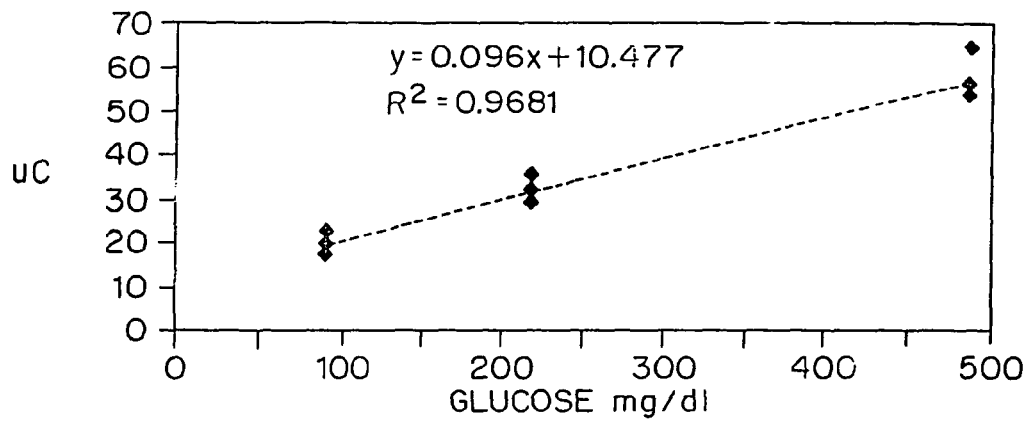
FIGS. 3A-3C show the current measured as a function of glucose concentration for three different hematocrit levels.
Figure 3B:
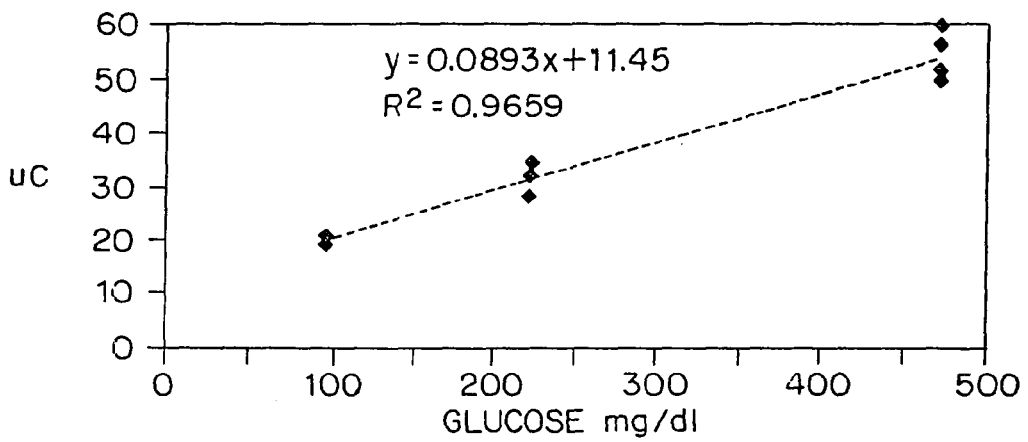
Figure 3C:
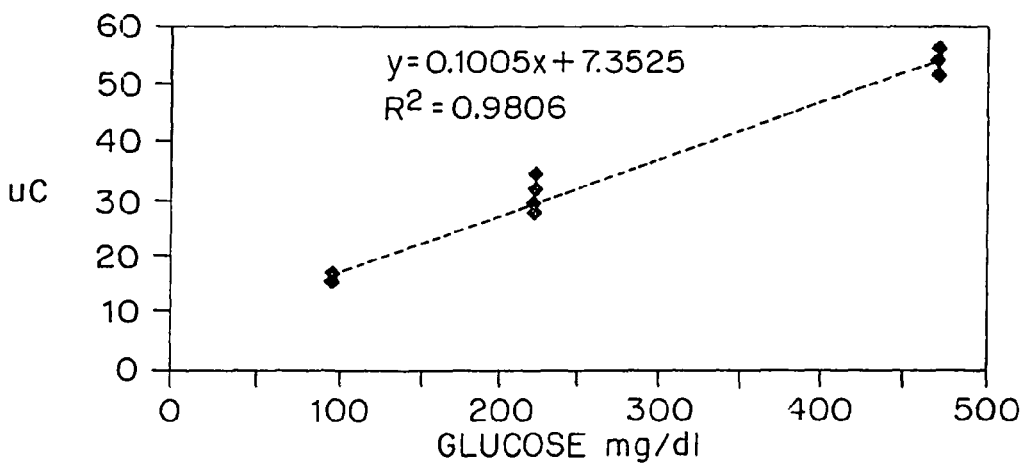

Test strips manufactured using the ink formulation of Example 1 in the manner described in Example 2 were placed in a test meter with an applied voltage of 500 mV and used to test blood samples having varying glucose concentrations and hematocrits ranging from 40% to 60%. FIGS. 3A-3C show the current measured 25 seconds after applying the voltage as a function of the glucose concentration, and FIG. 4 plots the slope of the glucose response as a function of hematocrit. As can be seen, the indicators produce highly reproducible current levels which are essentially independent of hematocrit.

EXAMPLE 4

Glucose test strips in accordance with the invention were made in accordance with Example 2, except the non-conductive layer was formed with 7 g Spherisorb C4 and 1 g Cab-o-Sil TS610. This formulation was laid down on three different types of carbon-containing conductive elements as follows:
  A: Ercon EC1
  B: Ercon EC2
  C: Ercon EC2 on top of Acheson Carbon, Electrodag 423 SS.

Figure 5A:
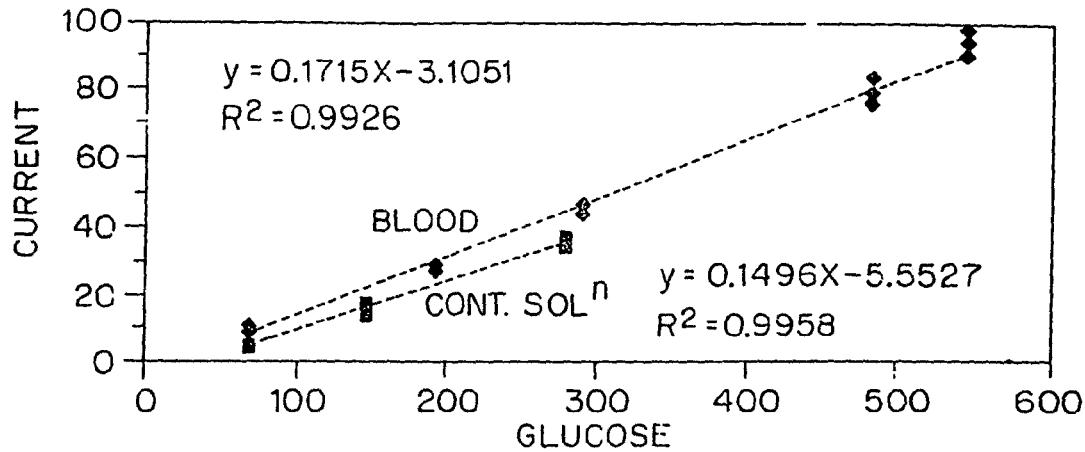
FIGS. 5A-5C show the current measured as a function of glucose in blood and a control solution for three different conductive elements.
Figure 5B:
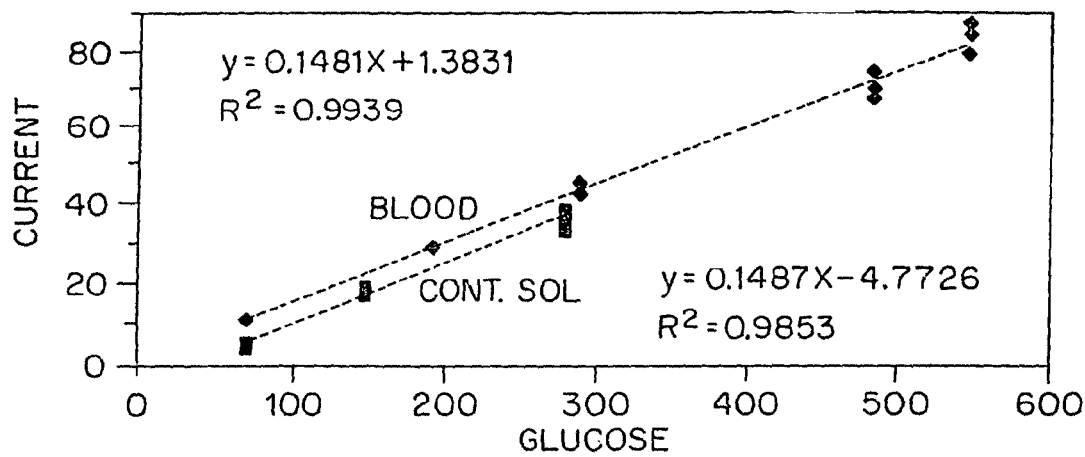
Figure 5C:
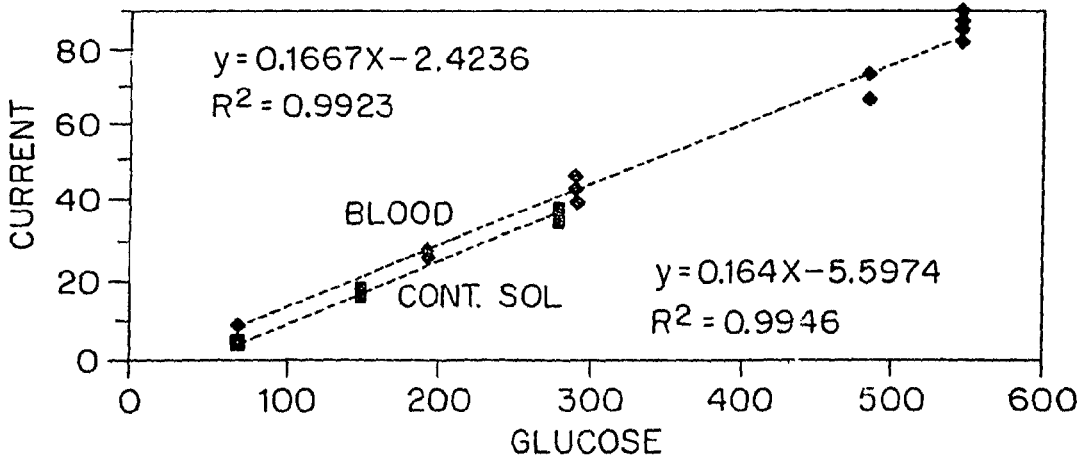

These test strips were used to measure varying levels of glucose in either a control solution (One Touch Control Solution, Lifescan Inc.) containing glucose in an inert solution or in blood at an applied voltage of 425 mV. The current observed 25 seconds after the voltage was applied was measured. FIGS. 5A-5C show the results obtained for the three formulations, A, B, and C, respectively. In all cases, the slope of the line showing the response of the meter to different glucose concentrations was essentially the same whether the measurements were made in blood or the control solution. Thus, this further demonstrates the independence of the test strips of the invention from the oxygen content and hematocrit of the sample, as well as the ability to sue various materials as the conductive element.

EXAMPLE 5

Test strips prepared in accordance with Example 2 were tested at two different sample temperatures, namely 37° C. and 20° C. using an applied voltage of 425 mV. FIGS. 6A and 6B show the current measured 25 seconds after applying the voltage as a function of glucose concentration. As can be seen, the slopes of the two lines are essentially identical (0.1068 at 20° C. versus 0.1009 at 37° C.), thus demonstrating that the test strips provide essentially temperature-independent behavior over a temperature range from ambient to physiological temperatures.

EXAMPLE 6

Figure 8A:
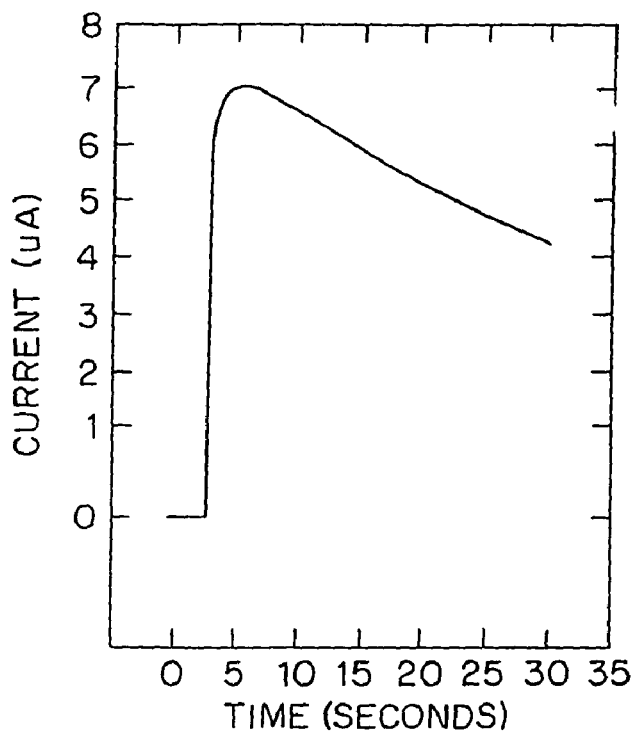
FIGS. 8A and 8B show current transients observed using a test strip according to the invention and a commercial carbon-based test strip.
Figure 8B:
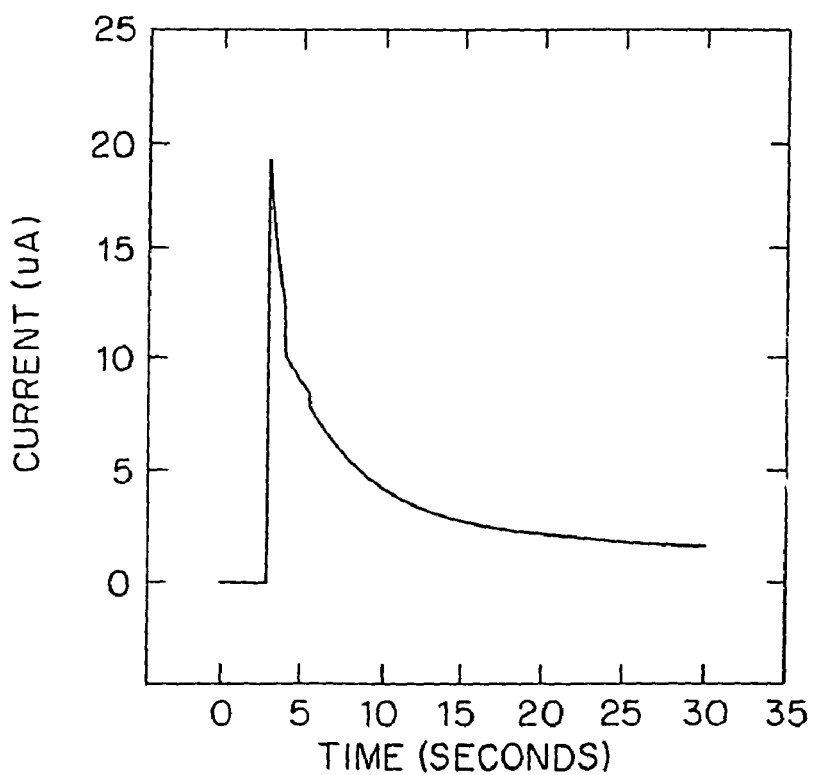

The current transient was measured for a test strip prepared in accordance with Example 2 and for a commercial test strip made with a carbon-containing ink. The results are shown in FIGS. 8A and 8B. As shown, the test strip of the invention (FIG. 8A) provides a very flat transient which maintains more than 50% of the peak current for a period of more than 25 seconds after the initial response from the test strip. In contrast, the carbon-based electrode exhibited an almost immediate decay in the current, having lost 50% of the peak current in a period of the first 1 to 2 seconds after the initial response from the test strip. This makes timing of the measurement difficult if peak current values are to be captured, or reduces the dynamic range of the meter if current must be measured after substantial decay has occurred. Thus, the test strips of the invention are advantageous in that the current generated in response to a given amount of glucose decays by less than 50% in the 5 seconds following peak current generation.

EXAMPLE 7

An ink for printing glucose test strips in accordance with the invention was formulated as follows:
  67.8 g 20 mM Citrate buffer, pH 6
  0.68 g Polyvinyl alcohol (MW 85,000-146,000, 88% hydrolysed)
  0.68 g of Polyvinyl pyrrolidone-vinyl acetate
  0.42 g of Dow Corning DC1500 antifoam
  3.4 g of hydroxyethyl cellulose (Natrosol 250G, Hercules)
  5.5 g of surface modified silica (Cabo-Sil TS610, Cabot)
  1.5 g glucose oxidase
  20.0 g Potassium Ferricyanide.

EXAMPLE 8

FIGS. 10A-I shows the stepwise preparation of a test strip in accordance with the invention. As is apparent from a comparison of this test strip and the strip of FIG. 1, the precise arrangement of the electrodes on the strip is not critical. Further, different materials may be used in fabricating the strip.

The first step in fabricating the test strip is the deposition of silver tracks 101, 102 of substrate 100. A preferred substrate is a 500 micron thick polyester film sold under the tradename Valox™. The silver electrodes can be formed by screen printing using an ink composition formulated as in Example 2.

Figure 10A:
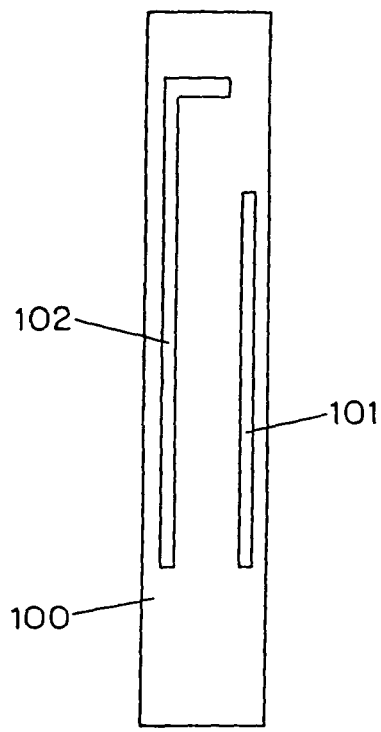
FIGS. 10A-10G show the manufacture of a test strip in accordance with the invention.
Figure 10B:
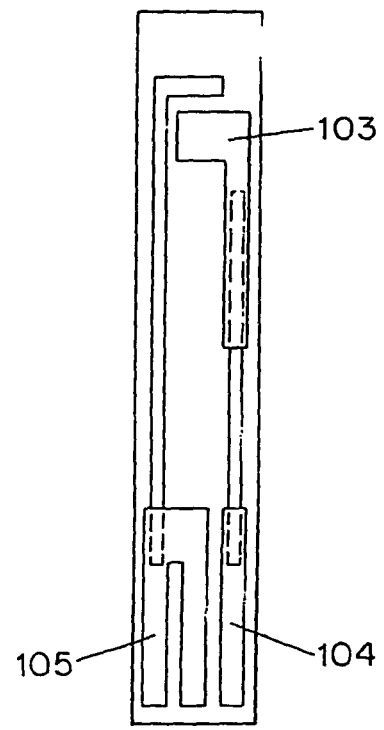
Figure 10C:
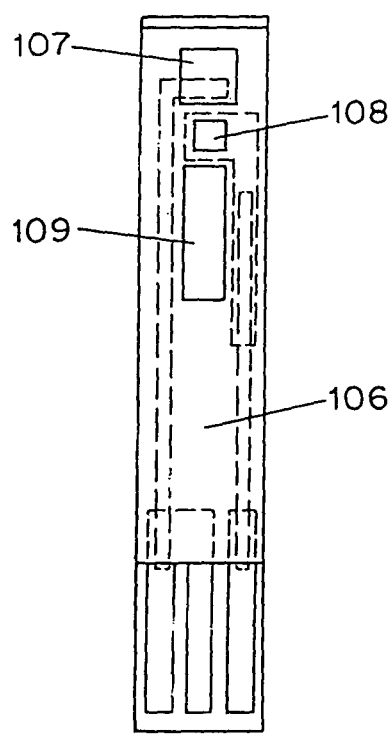

After deposition of the silver electrodes, a second electrode print is carried out to form carbon conductive elements 103, 104 and 105 as shown in FIG. 10B. Conductive element 103 is formed in contact with silver track 101 and will form the working electrode in the finished test strip. Carbon pads 104 and 105 connect electrically to the ends of silver tracks 101 and 102 and provide connection between the strip and a test meter. The carbon conductive elements can be formed by screen printing with a conductive carbon ink formulation such as those described in the previous examples.

The next step in the manufacturing process is the deposition of an insulation layer 106 for example by screen printing an insulation ink, for example the dielectric ink of Example 2. (FIG. 10C) As shown, the insulation layer contains three windows 107, 108 and 109. Window 108 is aligned with the end of the carbon conductive element 103. Window 107 is aligned with the end of silver track 102 to provide access to the reference electrode. The third window, 109, is provided to permit passage of insulation material from the second insulation coating through the mesh layer, but is not required.

Figure 10D:
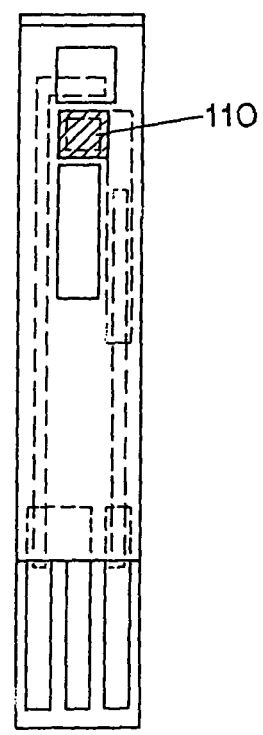
Figure 10E:
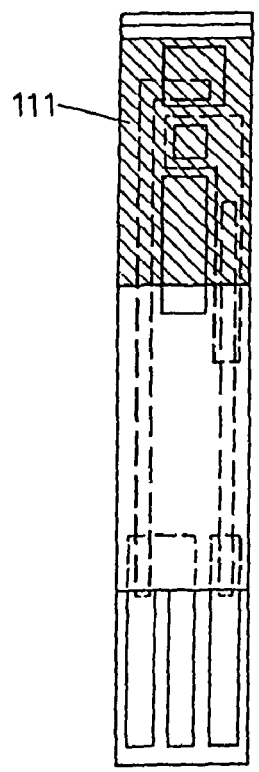

FIG. 10D shows the next step in the process, which is the formation of an integrated reagent/blood separation layer 110. This layer is deposited over window 108 and extends over the insulation layer 106 along all sides of the window 108. A suitable formulation for printing layer 110 has the following composition to provide an integrated reagent/blood separation layer with a buffered pH of about 6:

| Component | Amount |
| --- | --- |
| Analar Water | 3 L |
| Tri-sodium Citrate | 15.75 g |
| Nat 250 G | 150 g |
| Citric Acid | 6.3 g |
| Poly Vinyl Alcohol | 30 g |
| DC 1500 Defoamer | 15 ml |
| Cabosil | 225 g |
| Glucose Oxidase | 48 g |
| Potassium Hex/60299 | 660 g |
| PVPVA | 30 g |

After the integrated reagent/blood separation layer 110 is formed, a layer of mesh 111 is deposit over the sample collection region of the test strip. (FIG. 10E) The mesh 111 is preferably a nylon mesh which has been pretreated with acetone and Fluorad FC 170C surfactant to render the mesh hydrophilic. The purpose of the mesh 111 is the transport of the liquid sample evenly through the area between the working and reference electrodes.

Figure 10F:
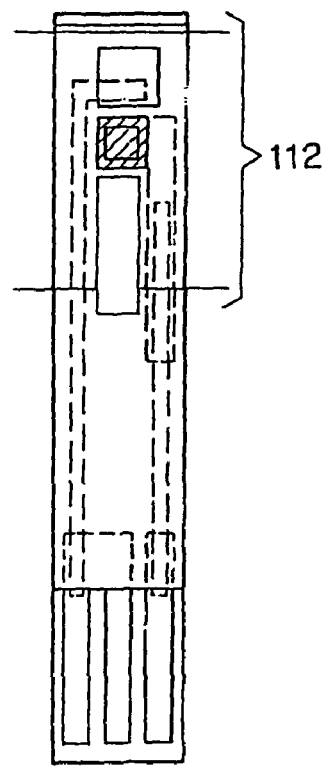
Figure 10G:
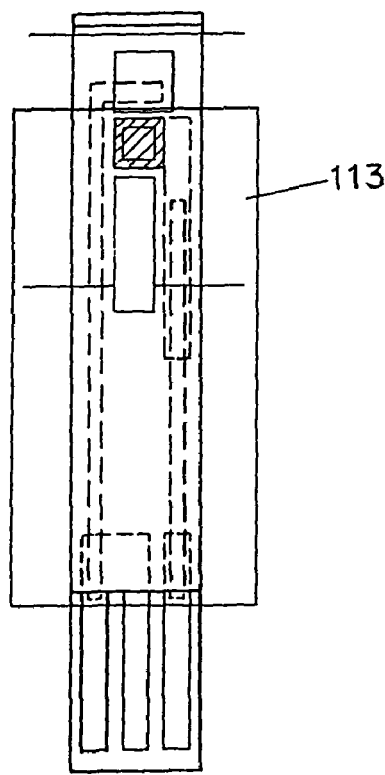

A second insulation print 112 is then carried out using a slightly more flexible insulation ink (ERCON Insulayer 820202) to define the sample collection region. (FIG. 10F). A tape cover 113 is then applied over the top of the test strip as described above in Example 2 to form a finished test strip. (FIG. 10G).

The invention claimed is:

1. A disposable test strip for use in a test meter which receives a disposable test strip and a sample of blood and performs an electrochemical analysis of the amount of a blood analyte in the sample, comprising:
   (a) a substrate;
   (b) a first conductive element disposed on the substrate;
   (c) a second conductive element disposed on the substrate in sufficient proximity to the first conductive element to allow the completion of an electrical circuit between the first and second conductive elements when a sample of blood is placed on the test strip;
   (d) a non-conductive integrated reagent/blood separation layer disposed over the first conductive element, the integrated reagent/blood separation layer comprising reagents for the electrochemical detection of the analyte dispersed in a non-conductive matrix effective to exclude blood cells from the surface of the first conductive element while permitting access to the first conductive element by soluble electroactive species;
   (e) contacts for making an electrical connection between the first and second conductive elements and the test meter; and
   (f) an insulation layer disposed over at least the first conductive element, the insulation layer having a first aperture therein aligned with the first conductive element, the insulation layer having a peripheral portion adjacent to a surrounding area of the first aperture, wherein the non-conductive integrated reagent/blood separation layer is formed covering the entire first aperture and the peripheral portion.

2. The disposable test strip of claim 1, wherein a sufficient amount of the peripheral portion is covered by the non-conductive integrated reagent/blood separation layer to reduce variation in a measured signal as a result of lateral diffusion away from the first aperture.

3. The test strip of claim 1, wherein the integrated reagent/blood separation layer comprises an enzyme for oxidation of glucose and a redox mediator effective to transfer electrons from the enzyme to the first conductive element.

4. The test strip of claim 3, wherein the matrix comprises silica having both hydrophobic and hydrophilic surfaces.

5. The test strip according to claim 4, wherein the integrated reagent/blood separation layer is formed from an aqueous composition comprising 2 to 10% by weight of a binder; 3 to 10% by weight of silica; 8 to 20% by weight of the redox mediator; and 1000 to 5000 units of the enzyme per gram of the aqueous composition.

6. The test strip according to claim 5, wherein the enzyme is glucose oxidase.

7. The test strip according to claim 5, wherein the redox mediator is ferricyanide.

8. The test strip according to claim 3, wherein the enzyme is glucose oxidase.

9. The test strip according to claim 3, wherein the redox mediator is ferricyanide.

10. The test strip of claim 1, wherein the first and second conductive elements comprise conductive carbon.

* * * * *